(12) United States Patent
Saab

(10) Patent No.: US 10,835,170 B2
(45) Date of Patent: Nov. 17, 2020

(54) METHODS FOR DETECTING NEURONAL OSCILLATION IN THE SPINAL CORD ASSOCIATED WITH PAIN AND DISEASES OR DISORDERS OF THE NERVOUS SYSTEM

(71) Applicant: Rhode Island Hospital, Providence, RI (US)

(72) Inventor: Carl Saab, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 348 days.

(21) Appl. No.: 15/751,416

(22) PCT Filed: Aug. 11, 2016

(86) PCT No.: PCT/US2016/046544
§ 371 (c)(1),
(2) Date: Feb. 8, 2018

(87) PCT Pub. No.: WO2017/027703
PCT Pub. Date: Feb. 16, 2017

(65) Prior Publication Data
US 2018/0228421 A1    Aug. 16, 2018

Related U.S. Application Data

(60) Provisional application No. 62/203,798, filed on Aug. 11, 2015.

(51) Int. Cl.
*A61B 5/00* (2006.01)
*A61N 1/36* (2006.01)
(Continued)

(52) U.S. Cl.
CPC .......... *A61B 5/407* (2013.01); *A61B 5/04001* (2013.01); *A61B 5/7257* (2013.01);
(Continued)

(58) Field of Classification Search
CPC ... A61B 5/407; A61B 5/04001; A61B 5/7257; A61B 5/0478; A61B 5/048; A61N 1/36021; A61N 1/36002; A61N 1/36071
See application file for complete search history.

(56) References Cited

U.S. PATENT DOCUMENTS 6,067,467 A    5/2000   John
8,185,207 B2   5/2012   Molnar et al.
(Continued)

OTHER PUBLICATIONS

Amir et al., "Membrane potential oscillations in dorsal root ganglion neurons: role in normal electrogenesis and neuropathic pain," J Neurosci. 19(19):8589-96 (1999).
(Continued)

*Primary Examiner* — Max F Hindenburg
(74) *Attorney, Agent, or Firm* — Clark & Elbing LLP (57) ABSTRACT

Disclosed are methods for detecting neuronal oscillation in the spinal cord of a subject. The methods can be utilized to determine that the subject has a disease or disorder of the spinal cord. The methods are useful for treating or reducing the likelihood of pain in a subject by detecting neuronal oscillation in the spinal cord and, e.g., administering a therapeutic agent to the subject. The electrode (LFP) methods disclosed herein may also be utilized to screen for a therapeutic agent that decreases neuronal oscillation in the spinal cord using a non-human animal subject.

19 Claims, 4 Drawing Sheets

(51) Int. Cl.
*A61B 5/04* (2006.01)
*A61B 5/0478* (2006.01)
*A61B 5/048* (2006.01)

(52) U.S. Cl.
CPC ..... *A61N 1/36021* (2013.01); *A61N 1/36071* (2013.01); *A61B 5/048* (2013.01); *A61B 5/0478* (2013.01); *A61N 1/36002* (2017.08)

(56) References Cited

U.S. PATENT DOCUMENTS

| | | | |
|---|---|---|---|
| 8,359,102 B2 | 1/2013 | Alataris et al. | |
| 8,423,147 B2 | 4/2013 | Alataris et al. | |
| 8,694,087 B2 | 4/2014 | Schiff | |
| 8,989,859 B2* | 3/2015 | Deem | A61N 1/0412 422/81 |
| 9,113,801 B2* | 8/2015 | DiLorenzo | A61B 5/04001 |
| 9,180,287 B2* | 11/2015 | Gonzalez | A61N 1/0452 |
| 9,295,396 B2* | 3/2016 | Gharib | A61B 5/0488 |
| 9,393,416 B2* | 7/2016 | Rooney | A61N 1/0531 |
| 9,409,023 B2* | 8/2016 | Burdick | A61N 1/0553 |
| 2009/0062676 A1* | 3/2009 | Kruglikov | A61B 5/0484 600/544 |
| 2011/0251583 A1* | 10/2011 | Miyazawa | A61N 1/36071 604/503 |
| 2012/0109241 A1 | 5/2012 | Rauscher | |

OTHER PUBLICATIONS

Buzsaki, "Two-stage model of memory trace formation: a role for "noisy" brain states," Neuroscience. 31(3):551-570 (1989).

de Vries et al., "Altered resting state EEG in chronic pancreatitis patients: toward a marker for chronic pain," J Pain Res. 6:815-824 (2013).

Deumens et al., "Early spread of hyperexcitability to caudal dorsal horn networks after a chemically-induced lesion of the rat spinal cord in vitro," Neuroscience. 229:155-163 (2013).

Hains et al., "Alterations in Burst Firing of Thalamic VPL Neurons and Reversal by Nav1.3 Antisense After Spinal Cord Injury," J Neurophysiol. 95(6):3343-3352 (2006).

Herbert et al., "Altered brain wave activity in persons with chronic spinal cord injury," Int J Neurosci. 117(12):1731-1746 (2007).

International Search Report and Written Opinion for International Application No. PCT/US2016/046544, dated Oct. 26, 2016 (14 pages).

Jensen et al., "Steps Toward Developing an EEG Biofeedback Treatment for Chronic Pain," Appl Psychophysiol. Biofeedback. 38(2):101-108 (2013).

Koulousakis et al., "Neuromodulation in chronic pain after Spine-Surgery," Eur Spine J. 18:1713-1826 (2009) (1 page).

Leblanc, "Cortical Theta Is Increased While Thalamocortical Coherence Is Decreased in Rat Models of Acute and Chronic Pain," Pain. 155(4):773-82 (2014).

Liu et al., "Hyperexcitability in sensory neurons of rats selected for high versus low neuropathic pain phenotype," Neuroscience. 105(1):265-275 (2001).

Liu et al., "Spinal Nerve Injury Enhances Subthreshold Membrane Potential Oscillations in DRG Neurons: Relation to Neuropathic Pain," J Neurophysiol. 84(1):205-215 (2000).

Ngernyam et al., "The effects of transcranial direct current stimulation in patients with neuropathic pain from spinal cord injury," Clinical Neurophys. 126(2):382-390 (2015).

Saab, "Pain-related changes in the brain: diagnostic and therapeutic potentials," Trends in Neurosci. 35(10):629-637 (2012).

Song et al., "Evoked bursting in injured A BETA dorsal root ganglion neurons: A mechanism underlying tactile allodynia," Pain. 153(3):657-665 (2012).

Svoboda et al., "Detection of Cortical Oscillations Induced by SCS Using Power Spectral Density," Radioengineering. 16(4):38-45 (2007).

Wang et al., "Gamma oscillation by synaptic inhibition in a hippocampal interneuronal network model," J Neurosci. 16(20):6402-6413 (1996).

Wydenkeller et al., "Neuropathic pain in spinal cord injury: significance of clinical and electrophysiological measures," Eur J Neurosci. 30(1):91-99 (2009).

* cited by examiner

METHODS FOR DETECTING NEURONAL OSCILLATION IN THE SPINAL CORD ASSOCIATED WITH PAIN AND DISEASES OR DISORDERS OF THE NERVOUS SYSTEM

CROSS REFERENCE TO RELATED APPLICATIONS

This application claims priority to U.S. Provisional Patent Application No. 62/203,798, filed on Aug. 11, 2015, the entirety of which is incorporated herein by reference.

FIELD OF THE INVENTION

The invention features methods for detecting neuronal oscillation in the spinal cord, particularly for the diagnosis and treatment of pain and diseases or disorders of the peripheral and central nervous system.

BACKGROUND OF THE INVENTION

Oscillation is an essential mode of communication between neuronal ensembles. Recordings of brain activity invariably feature oscillation at multiple frequencies. Brain oscillation is thought to require cortical layer hierarchy and recruitment of subcortical structures, such as the thalamus. Neuronal oscillation in the central pattern generator circuitry has been described in the spinal cord ventral horn in regards to locomotion in vivo. Moreover, in silico modeling suggests a critical number of neurons with synchronized firing is required to generate oscillatory 'waves' traveling over short (within network) and long (between networks) distances. Thus, neuronal oscillation plays a crucial, though as of yet incompletely defined, role in health and disorders of thought and cognition, such as autism and schizophrenia.

Recent studies have shown that oscillation in the primary somatosensory cortex (S1) is modulated in humans, as well as in rat models of both acute and chronic pain. In rats, acute pain increased local field potential (LFP) power in the theta frequency band transiently, whereas chronic constriction injury of the sciatic nerve (CCI, chronic pain) evoked a long-term (up to 14 days) increase in theta power. Thus, brain oscillation is modulated as a function of sensory states relevant to pain.

Pain is a major symptom in many medical conditions and can significantly interfere with a subject's quality of life and general functioning. The financial burden associated with chronic pain in the United States is estimated to be greater than $100 billion a year, due to decreased productivity and medical expenses. Accordingly, there exists a need in the medical field to develop safe and effective methods of detecting pain and the use of these methods to determine efficacious therapies for the diverse diseases and disorders associated with pain. Thus, methods capable of detecting and monitoring pain are highly desirable.

SUMMARY OF THE INVENTION

A first aspect of the invention features a method for detecting neuronal oscillation in the spinal cord of a subject, the method including: a) recording local field potential (LFP) waveforms in the spinal cord of the subject; b) applying fast Fourier transfer (FFT) to convert LFP waveforms from the time domain to the frequency domain, thereby producing a power spectral density (PSD) histogram; c) assessing frequency bands of the PSD histogram (e.g., pre-defined bands (e.g., theta, alpha, beta, and/or gamma frequency bands) or a newly identified band); and d) determining that said subject has a disease or disorder associated with the spinal cord, wherein an increase of one or more of said frequency bands from baseline, absence or occurrence of newly identified frequency bands, and/or shifts in peak amplitude or peak latency serves as an indicator of said disease or disorder.

In some embodiments, the method further includes assessing other indicators of said disease or disorder, upon conversion of LFP to the frequency domain. Other indicators may include, but are not limited to, signal coherence and/or cross frequency coupling or Granger causality between frequency bands in distinct spinal cord regions on the rostra-caudal axis (e.g. cervical and lumbar), laterally in the spinal cord (e.g. left to right) or between the spinal cord and the brain.

In various embodiments, the method further includes administering a therapeutic agent to the subject. In some embodiments, the method further includes titrating or determining an effective amount of the therapeutic agent. In preferred embodiments, an effective amount results in an amelioration or stabilization of the disease or disorder in the subject, such that there is a decrease of one or more of the frequency bands or other indicators discussed above relative to baseline after administering the therapeutic agent. In particular embodiments, steps (a)-(c) of the method are repeated after administration of the therapeutic agent.

In various embodiments, the disease or disorder associated with the spinal cord is selected from the group consisting of spinal cord ischemia, spinal cord convulsions, spinal cord infarction, spinal cord injury, disc herniation, multiple sclerosis, muscular dystrophy, amyotrophic lateral sclerosis, demyelinating diseases, bladder inflammation, irritable bowel syndrome, inflammatory bowel disease, breathing disorders, and esophageal disorders.

In some embodiments, the subject is a mammal. In certain embodiments, the subject is a human.

A second aspect of the invention features a method of treating or reducing the likelihood of pain in a subject by detecting neuronal oscillation in the spinal cord, the method including: a) recording LFP waveforms in the spinal cord of the subject; b) applying FFT to convert LFP waveforms from the time domain to the frequency domain, thereby producing a PSD histogram; c) assessing frequency bands (e.g., theta, alpha, beta, gamma, and/or a newly identified band) of the PSD histogram (or other indicators discussed above); and d) administering a therapeutic agent to said subject, if there is an increase of one or more of said frequency bands from baseline, absence or occurrence of newly identified frequency bands, and/or shifts in peak amplitude or peak latency.

In some embodiments, the method further includes determining an effective amount of the therapeutic agent. In preferred embodiments, an effective amount results in an amelioration or stabilization of pain in said subject, wherein there is a decrease, modulation, or reversal to normal of one or more of said frequency bands, absence or occurrence of newly identified PSD peaks, and/or shifts in peak amplitude or peak latency relative to baseline after administering said therapeutic agent. In particular embodiments, steps (a)-(c) of the method are repeated after administration of the therapeutic agent. In certain embodiments, the method further includes administering one or more additional therapeutic agents to the subject.

In various embodiments, determining may be performed one or more times a second (e.g., using alternating current (AC) stimulation)) an hour, one or more times a day, or one or more times a month.

In some embodiments, determining is performed on a subject during surgical intraoperative procedures, awake light sedation, unconscious deep anesthesia, or a non-communicating vegetative state. In certain embodiments, determining is performed on a pediatric neonate subject.

In some embodiments, the pain is chronic pain. In various embodiments, the chronic pain is selected from the group consisting of neuropathic pain, headache, migraine headache, chronic tension type headache, migraine with allodynia, joint pain, sinus pain, muscle pain, nerve pain, shoulder pain, pelvis pain, neck pain, back pain, arthritis, fibromyalgia, shingles, nerve damage, cancer, post-stroke pain, spinal cord injury, an inflammatory disease, reperfusion injury, inflammatory bowel disease, irritable bowel syndrome, bladder pain, referred pain, and head trauma. In particular embodiments, the neuropathic pain is selected from the group consisting of diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathys, mono-neuropathies, and central pain syndrome.

In alternative embodiments, the pain is acute pain, e.g., nociceptive pain or post-operative pain.

In some embodiments, the subject is a mammal. In certain embodiments, the subject is a human.

A third aspect of the invention features a method of screening for a therapeutic agent that decreases, modulates, or reverses neuronal oscillation in the spinal cord using a non-human animal subject, the method including: a) administering an agent to the subject that modulates neuronal oscillation; b) recording LFP waveforms in the spinal cord; c) applying FFT to convert LFP waveforms from the time domain to the frequency domain, thereby producing a PSD histogram; d) assessing frequency bands (e.g., theta, alpha, beta, gamma, and/or newly identified frequency bands) of the PSD histogram; e) administering a test therapeutic agent to the subject; and f) repeating steps (b)-(d), such that a decrease of one or more of said frequency bands, absence or occurrence of new frequency bands, and/or shifts in peak amplitude or peak latency relative to baseline indicates that said test therapeutic agent decreases, modulates, or reverses neuronal oscillation in said subject.

In some embodiments, the neuronal oscillation is indicative of pain. In other embodiments, the subject has a disease or disorder associated with the spinal cord.

In some embodiments, the subject is a mammal.

In any of the foregoing aspects, LFP waveforms may be recorded with one or more sensors positioned in the spinal cord of the subject. In various embodiments, the one or more sensors includes one or more electrodes.

In any of the foregoing aspects, LFP waveforms may be recorded with one or more sensors attached to the skin of the subject. In various embodiments, the one or more sensors includes one or more electrodes.

In any of the foregoing aspects, LFP waveforms may be recorded at sampling frequencies between about 2 Hz to about 35,000 Hz. In preferred embodiments, LFP waveforms are recorded at sample frequencies between about 10 Hz to about 300 Hz (e.g., 125 Hz).

In any of the foregoing aspects, the method may further include recording brain activity of the subject. In certain embodiments, brain activity may be recorded by electroencephalogram (EEG), magnetoencephalography (MEG), functional magnetic resonance imaging (fMRI), or positron emission tomography (PET).

In any of the foregoing aspects, the method may further include treating the subject with a neuromodulatory system. In certain embodiments, the neuromodulatory system includes a transcranial direct current stimulation system, transcranial magnetic stimulation system, deep brain stimulation system, ultrasound stimulation system or spinal cord stimulation system. In other embodiments, the neuromodulatory system may include a transdermal patch or intrathecal drug delivery pump.

In any of the foregoing embodiments, LFP waveforms may be recorded in the spinal cord dorsal horn of said subject.

Definitions

As used herein, the phrase "neuronal oscillation" refers to rhythmic or repetitive neural activity in the central nervous system or peripheral nervous system. Neural tissue can generate oscillatory activity in many ways, driven either by mechanisms within individual neurons or by interactions between neurons. Neuronal oscillation may be detected with invasive methods (e.g., intraoperative or implantable sensors) or non-invasive methods (e.g., electrodes attached to the skin of a subject). It may be detected using electrophysiological methods (e.g. recording electrodes connected to amplifiers) or using various sensors that sense neuronal activity directly (e.g. voltage sensitive dyes) or indirectly (e.g. BOLD fMRI or magnetic field).

As used herein, the phrase "local field potential" or "LFP" refers to an extracellular measurement that represents the aggregate activity of a population of neurons. Measurements of LFP waveforms may be used to determine neuronal oscillations in the peripheral nervous system or the central nervous system, e.g., the brain and spinal cord.

As used herein, the phrase "fast Fourier transfer" or "FFT" is an algorithm used to convert waveforms from the time domain to the frequency domain. FFT may be implemented using a computing program including a computing language, e.g., MATLAB® (MathWorks), and/or a computing language, e.g., C, C++, Java, Fortran, or Python.

As used herein, "power spectral density" or "PSD" refers to the numerical or visual representation (e.g., histogram) of the distribution of the power amplitude of a waveform as a function of frequency. Specific frequency bands may be evaluated using PSD, which include, but are not limited to, theta (e.g., 4-8 Hz), alpha (e.g., 8-12 Hz), beta (e.g., 12-25 Hz) and gamma (e.g., 25-100 Hz) frequency bands. Analysis of PSD outside of standard frequency bands (e.g. 6-15 Hz, 100-3000 Hz)) may also be evaluated using the methods described herein.

As used herein, "signal coherence" refers to the magnitude squared coherence as a measure of power transfer between stochastic systems. The output of the function yields coherence values between 0 and 1, with a value of 1 signifying 100% perfectly matching amplitude difference between two waveforms at the observed frequency.

As used herein, "cross-frequency coupling" refers to phase-amplitude coupling as a measure of cross-frequency synchronization of one wavelength with the envelope of a second higher frequency wavelength.

As used herein, "Granger causality" refers to the putative direction of information flow within a circuit. The application of Granger causality in the frequency domain was developed via Fourier transform to estimate the relative strengths of influence between two sites in both directions and at different frequencies. The Granger causality at each frequency is thus defined by the ratio of predicted power to total power, and the GC spectrum can be viewed in terms of the fraction of the variance in one time series that can be attributed to another.

As used herein, "chronic pain" refers to a type of pain that lasts longer than three to six months and/or pain that extends beyond the expected period of tissue healing. Chronic pain may originate with an initial trauma/injury or infection, or may be an ongoing cause of pain associated with neuropathic pain (e.g., diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome), headaches, joint pain, backaches, sinus pain, muscle pain, nerve pain, and pain affecting specific parts of the body, such as shoulders, pelvis, and neck. Chronic pain may also be associated with lower back pain, arthritis, multiple sclerosis, fibromyalgia, shingles, nerve damage, or cancer.

As used herein, "acute pain" refers to a type of pain that typically lasts less than three to six months and/or pain that is directly related to soft tissue damage. Acute pain may follow non-neural tissue injury, for example, tissue damage from surgery or inflammation. Acute pain is of short duration, but it gradually resolves as the injured tissues heal.

As used interchangeably herein, the terms "subject" and "patient" refer to any animal (e.g., a mammal, e.g., a human). A subject to be treated or tested for responsiveness to a therapy according to the methods described herein may be one who has been diagnosed with pain or a disease, disorder, or condition of the spinal cord.

As used herein, the term "modulate" refers to the ability to cause an overall decrease or increase preferably of 20% or greater, more preferably of 50% or greater, and most preferably of 75%, 85%, 90%, 95%, or greater compared to baseline.

As used herein, the terms "reverse" refer to the ability to cause an overall return to baseline (i.e., normalcy or before disease) most preferably of 75%, 85%, 90%, 95%, or greater compared to 100% baseline.

As used interchangeably herein, the terms "decrease" and "reduce" refer to the ability to cause an overall decrease preferably of 20% or greater, more preferably of 50% or greater, and most preferably of 75%, 85%, 90%, 95%, or greater. Decrease or reduce may refer to, e.g., the symptoms of the disease, disorder, or pain in general or the determination of frequency bands as detected by the methods disclosed herein.

As used herein, "treating" refers to administering a pharmaceutical composition for prophylactic and/or therapeutic purposes. To "reduce the likelihood" refers to prophylactic treatment of a patient who is not yet ill, but who is susceptible to, or otherwise at risk of, a particular disease or condition (e.g., the conditions described herein, such as pain (e.g., chronic or acute pain)). To "treat disease" or use for "therapeutic treatment" refers to administering treatment to a patient already suffering from a disease to ameliorate the disease and improve the patient's condition. The term "treating" also includes treating a patient to delay progression of a disease or its symptoms. Thus, in the claims and embodiments, treating is the administration to a patient either for therapeutic or prophylactic purposes. Beneficial or desired results can include, but are not limited to, alleviation, amelioration, or prevention of a disease, a disorder, a condition, or one or more symptoms associated with a disease, a disorder, or a condition; diminishment of extent of disease, disorder, or condition; stabilization (i.e., not worsening) of a disease, disorder, or condition; delay or slowing the progress of a disease, disorder, or condition; and palliation of a disease, disorder, or condition.

As used herein, "prevention" refers to a prophylactic treatment is given to a subject who has or will have a disease, a disorder, a condition, or one or more symptoms associated with a disease, a disorder, or a condition.

As used herein, "therapeutic agent" refers to any agent that produces a healing, curative, stabilizing, or ameliorative effect. An "agent" may also be used to, e.g., stimulate or cause or a response in the subject, e.g., neuronal oscillation in the central nervous system, e.g., spinal cord, e.g. feedback system (including neurofeedback system).

As used herein, "electrode" refers to an electric conductor through which an electric current enters or leaves an electrolytic cell or other medium. It further refers to the geometric configuration of discrete type electrical conductive elements capable of causing an electromagnetic field when a current and voltage is applied. The electrode can be of any shape, and can be symmetrically or asymmetrically configured. Size and shape depend on the specific requirements of the application.

The abbreviation "EEG," as used herein, refers to electroencephalogram.

The abbreviation "MEG," as used herein, refers to magnetoencephalography.

The abbreviation "fMRI," as used herein, refers to functional magnetic resonance imaging.

The abbreviation "PET," as used herein, refers to positron emission tomography.

The recitation herein of numerical ranges by endpoints is intended to include all numbers subsumed within that range (e.g., a recitation of 1 to 5 includes 1, 1.5, 2, 2.75, 3, 3.80, 4, and 5).

As used herein, "about" refers to an amount ±10 of the recited value.

As used herein, "a" or "an" means "at least one" or "one or more" unless otherwise indicated. In addition, the singular forms "a," "an," and "the" include plural referents unless the context clearly dictates otherwise. Thus, for example, reference to a composition containing "a therapeutic agent" includes a mixture of two or more therapeutic agents.

Other features and advantages of the invention will be apparent from the following Detailed Description and from the claims.

DETAILED DESCRIPTION OF THE INVENTION

As discussed above, there is a lack of reliable methods available for detecting and monitoring pain, particularly for determining effective therapeutic agents for a variety of conditions, disorders, and diseases associated with pain. We have developed a method of detecting neuronal oscillation occurring in the spinal cord, which may be used as a reliable marker for pain-related plasticity. The methods disclosed herein may also be used for the diagnosis and treatment of non-pain conditions associated with the spinal cord. Furthermore, methods disclosed herein may be used to screen for therapeutic agents that decrease neuronal oscillation in the spinal cord, and are thus applicable to pain as well as diseases and disorders associated with the spinal cord.

Detection of Neuronal Oscillation in the Spinal Cord

Neuronal activity in a subject may be detected directly or indirectly at the level of local field potential (LFP). LFP is a good candidate for a "pain biomarker" as these extracellularly recorded signals are representative of a local network of neurons or neuronal population. Thus, analysis of LFP using a sensor, e.g., an electrode, allows for the study of multiple neuronal networks simultaneously. LFP waveforms may be recorded at sampling frequencies between about 2 Hz to about 35,000 Hz. Preferably, LFP waveforms are recorded at sample frequencies between about 10 Hz to about 300 Hz (e.g., 125 Hz). LFP waveforms may be recorded with one or more sensors (e.g., electrodes) positioned in the spinal cord of the subject or with one or more sensors (e.g., electrodes) attached to the skin of the subject. Other types of sensors include any sensor capable of detecting neuronal activity, e.g., calcium imaging, fMRI, MEG, MRI, and PET (acronyms defined below).

Neuronal oscillation may be detected with invasive methods (e.g., intraoperative or implantable sensors) or non-invasive methods (e.g., sensors, e.g., electrodes, attached to the skin of a subject). These methods may include detecting shifts in power spectral density (PSD) using fast Fourier transfer (FFT) analysis to determine the occurrence or absence of new spectral peaks, shifts in peak amplitudes or peak latency from a PSD histogram. Methods of detecting neuronal oscillation may further include the use of electroencephalogram (EEG) and magnetoencephalography (MEG) in addition to other types of imaging techniques and brain scans (for example, magnetic resonance imaging (MRI), functional magnetic resonance imaging (fMRI), positron emission tomography (PET), etc.) in combination with recording of LFP. Such techniques may be applied to a subject prior to, concurrently, or subsequent to recording of LFP.

Diagnostic Methods

The present invention provides methods for detecting neuronal oscillation in the spinal cord of a subject (e.g., a mammal, e.g., a human) indicative of pain or a disease or disorder associated with the spinal cord. Diagnostic methods feature the detection of neuronal oscillation in the spinal cord of a subject, e.g., as a biomarker for pain (e.g., chronic or acute pain) or diseases or disorders associated with the spinal cord. The neuronal activity patterns that make up the pain biomarker can be divided into two major categories: spontaneous (e.g., independent or temporally not associated with an overt stimulus or identifiable cause) and evoked (e.g., activity correlated with an overt stimulus or identifiable cause). Both forms of pain may be detected using these methods disclosed herein. The methods described herein for detection of neuronal oscillation in the spinal cord may be used for local assessment of pathology in the spinal cord (e.g. at the lumbar level), but may could also be used as a 'comparator' when sensors are placed at multiple levels of the spinal cord to assess the 'relative' state of pathology (e.g., sensors could be placed at lumbar, thoracic and cervical levels, as well as in the brain). In this case, the methods may be used in a 'differential' protocol whereby the area of pathology is localized, and the disease more accurately diagnosed, based on combinatorial or differential signal processing of LFP at several levels of the neuraxis simultaneously (e.g., "combined" cervical, lumbar and brain recordings using arithmetic or other mathematical methods).

Pain

Pain is associated with a wide range of medical conditions. The present invention features methods for diagnosing and treating a subject (e.g., a mammal, such as a human) with pain, e.g., conditions associated with pain. The methods of diagnosis and treatment disclosed herein are based, inter alia, on the inventor's discovery that neuronal oscillation in the spinal cord of a subject is indicative of pain, e.g., a biomarker for pain. Subjects diagnosed and treated using methods of the present invention may include subjects with acute pain, subacute pain, or chronic pain (e.g., pain that lasts longer than three to six months or pain that extends beyond the expected period of healing), and/or pain that originates from an initial trauma/injury or infection, or conditions associated with pain (e.g., post-herpetic neuralgia, trigeminal neuralgia, phantom limb pain, carpal tunnel syndrome, sciatica, pudendal neuralgia, complex regional pain syndrome, or central pain syndrome, headaches, in particular, migraine, joint pain, backaches, sinus pain, muscle pain, nerve pain, and pain affecting specific parts of the body, such as shoulders, pelvis, and neck, and/or pain that is associated with lower back pain, arthritis, headache, fibromyalgia, shingles, or nerve damage).

Methods described herein may be useful for the diagnosis, treatment, reduction, or prevention of various forms of pain, whether acute or chronic. Exemplary conditions that may be associated with pain include, for example, soft tissue, joint, bone inflammation and/or damage (e.g., acute trauma, osteoarthritis, or rheumatoid arthritis), myofascial pain syndromes (fibromylagia), headaches (including cluster headache, migraine, and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures).

The present invention provides methods for, e.g., detecting and treating inflammatory pain. Inflammatory pain is a form of pain that is caused by tissue injury or inflammation (e.g., in postoperative pain or rheumatoid arthritis). Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness associated with hypersensitivity to normally innocuous tactile stimuli), and/or spontaneous burning or shooting lancinating pain. In inflammatory pain, symptoms are apparent, at least initially, at the site of injury or inflamed tissues and typically accompany arthritis-associated pain, musculo-skeletal pain, and postoperative pain. The different types of pain may coexist or pain may be transformed from inflammatory to neuropathic during the natural course of the disease, as in post-herpetic neuralgia.

Other types of pain diagnosed, treated, reduced, or prevented with methods of the present invention include functional pain, e.g., conditions in which there is no obvious peripheral pathology or lesion to the nervous system. This particular form of pain is generated by abnormal function of the nervous system and conditions characterized by such pain include fibromyalgia, tension-type headache, and irritable bowel syndrome.

The present invention may also be useful for the diagnosis, treatment, reduction, or prevention of musculo-skeletal pain (after trauma, infections, and exercise), pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, hereditary conditions, central nervous system pain, such as pain due to spinal cord or brain stem damage, cerebrovascular accidents, tumors, infections, demyelinating diseases including multiple sclerosis, low back pain, sciatica, and post-operative pain.

Diseases and Disorders of the Spinal Cord

The invention also provides methods of diagnosing, treating, reducing, or preventing one or more diseases or disorders of the spinal cord in a subject or predicting the future severity of one or more diseases or disorders of the spinal cord by the steps of: recording LFP waveforms in the spinal cord of the subject, applying FFT to convert LFP waveforms from the time domain to the frequency domain, thereby producing a power spectral density PSD histogram, assessing frequency bands of the PSD histogram (e.g., theta, alpha, beta, and/or gamma as well as analysis of PSD outside of standard frequency bands); and determining that the subject has a disease or disorder associated with the spinal cord. In particular, an increase of one or more of the frequency bands from baseline serves as an indicator of the disease or disorder. Such methods may also be used to monitor the progression, severity, and development of one or more diseases or disorders of the spinal cord.

Diseases and disorders of the spinal cord that may be diagnosed, treated, prevented, or reduced according to the methods of the present invention may include, but are not limited to, spinal cord injury, spinal cord ischemia, spinal cord convulsions, spinal cord infarction, multiple sclerosis, muscular dystrophy, amyotrophic lateral sclerosis, demyelinating diseases, bladder inflammation, irritable bowel syndrome, inflammatory bowel disease, breathing disorders, and esophageal disorders. In particular, spinal cord injuries can include contusions (bruising of the spinal cord), compression (caused by pressure on the spinal cord), lacerations (severing or tearing of some nerve fibers), central cord syndrome (damage to the corticospinal tracts of the cervical region of the spinal cord), and paralysis (loss of control over voluntary movement and muscles of the body). The symptoms of spinal cord injury vary somewhat depending on the location of the injury. The method described above can also be used to detect pain of peripheral origin, or pain caused by damage to or disease of peripheral nerves, as sensory primary afferent nerves project to the spinal cord and could, therefore, modulate the spinal cord LFP.

Methods of Treatment

The present invention provides methods of treating a subject (e.g., a mammal, such as a human) by detecting neuronal oscillation in the spinal cord that include recording LFP waveforms in the spinal cord of the subject, applying FFT to convert LFP waveforms from the time domain to the frequency domain, thereby producing a PSD histogram, assessing theta, alpha, beta, and/or gamma frequency bands of the PSD histogram, and administering a therapeutic agent to the subject if there is an abnormal variation of one or more of the frequency bands (e.g., theta, alpha, beta, and/or gamma as well as analysis of PSD outside of standard frequency bands) from baseline, or shifts in peak amplitude or peak latency. Thus, the methods as described herein may result in a reduction in the likelihood of pain.

The methods of the present invention for detecting neuronal oscillation in the spinal cord may be performed on a subject within 24 hours (e.g., within 20 hours, 16 hours, 12 hours, 8 hours, 4 hours, 3 hours, 2 hours, or 1 hour) of an initial presentation of the subject to a medical professional. The method may also be performed at least 24 hours (e.g., at least 48 hours, 3 days, 4 days, 5 days, 6 days, or one week) after an initial presentation of the subject to a medical professional. The method may be performed on a subject previously admitted to a medical facility for a disease or disorder. The method may also be performed one or more (e.g., two, there, four, or five) times for treating a subject at intervals (e.g., hourly, daily, weekly, or monthly) or irregularly. The frequency of treatment may be determined based on the use of the methods disclosed herein to diagnose or to continuously monitor the state of LFP in the spinal cord (e.g. a sensor continuously monitoring LFP in a feedback system).

Upon assessing that there is a variation of one or more of the frequency bands (e.g., theta, alpha, beta, and/or gamma) from baseline, a therapeutic agent may be administered to the subject one or multiple times daily (e.g., two times, three times, up to four times a day), weekly (or at some other multiple day interval), or on an intermittent schedule, with that cycle repeated a given number of times (e.g., 2-10 cycles) or indefinitely. According to the methods described herein, therapeutic agents may also be administered chronically (e.g., more than 20 days, e.g., 21 days, 30 days, 60 days, 3 months, 6 months, 9 months, 1 year, 2 years, or 3 years). Sensors of the present method may also be coupled to an 'effector' (e.g. pharmacotherapy or neuromodulatory device) in an automated closed-loop system.

Dosing of Therapeutic Agents

Methods of the present invention may be used to determine the effective amount of the therapeutic agent (e.g., dosage or titration) for administration to treat or prevent the likelihood of pain in a subject (e.g., a mammal, such as a human) and/or to treat a disease or disorder associated with the spinal cord. An effective amount of the therapeutic agent results in, e.g., an amelioration or stabilization of pain or the disease or disorder of the spinal cord in the subject, such that there is a reversibility of one or more of frequency bands of the PSD relative to baseline after administering the therapeutic agent. Furthermore, the recording, applying, and assessing steps of the disclosed method may be repeated after administration of the therapeutic agent in order to determine an effective amount of the agent. These steps may be repeated one or more times an hour (e.g., within 1 minute, 5 minutes, 10 minutes, 15 minutes, 30 minutes, 45 minutes), day (e.g., within 12 hours, 8 hours, 4, hours, 2 hours, 1 hour), or month (e.g., at least 48 hours, 3 days, 4 days, 5 days, 6 days, or one week). Suitable therapeutic agents also include combinations thereof, such that one or more (e.g., two, three, four, or five or more) additional therapeutic agents is administered to the subject. When co-administered, the two therapeutic agents are desirably administered within 24 hours of each other (e.g., within 12 hours, 8 hours, 4, hours, 2 hours, 1 hour, 30 minutes, 15 minutes, or substantially simultaneously).

Actual dosage levels of the active ingredients in the therapeutic agents administered according to the present invention may be varied so as to obtain an amount of the active ingredient which is effective to achieve the desired response of treating or reducing the likelihood of pain in a subject, without undesirable side effects or being toxic to the subject. According to the methods of the present invention, the selected dosage level may be determined by the detection of neuronal oscillation in the spinal cord of a subject. For instance, assessment of biologically relevant frequency bands (e.g., theta, alpha, beta, and/or gamma) of the PSD histogram indicating a change (e.g., an increase or a decrease) in neuronal oscillation in the spinal cord upon administration of the therapeutic agent may be used to select the appropriate dosage.

The selected dosage level will also depend upon a variety of pharmacokinetic factors including the activity of the therapeutic agents, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. It is to be understood that, for any particular subject, specific dosage regimes should be adjusted over time according to the individual need and the professional judgment of the person administering or supervising the administration of the compound. For example, the dosage of a therapeutic agent can be increased if the lower dose does not provide sufficient activity to decrease frequency bands as assessed by the methods described herein. Conversely, the dosage of a therapeutic agent may be maintained or decreased if there is an appreciable decrease in theta, alpha, beta, and/or gamma frequency bands.

Therapeutic agents may include, pharmacological, non-pharmacological, and neuromodulatory agents (e.g. deep brain stimulation, spinal cord stimulation, transcranial current stimulation, transcranial magnetic stimulation, and ultrasound stimulation).

Methods of Screening Therapeutic Agents

The present invention features a methods of screening for a therapeutic agent using a non-human animal subject (e.g., mammal) that include administering an agent to the subject that increases neuronal oscillation, recording LFP waveforms in the spinal cord, applying FFT to convert LFP waveforms from the time domain to the frequency domain, thereby producing a PSD histogram, assessing frequency bands (e.g., theta, alpha, beta, and/or gamma as well as analysis of PSD outside of standard frequency bands) of the PSD histogram, administering a test therapeutic agent to the subject; and repeating the prior recording, applying, and assessing steps. Furthermore, a decrease of one or more of the frequency bands (e.g., theta, alpha, beta, and/or gamma) relative to baseline indicates that the test therapeutic agent decreases neuronal oscillation in the subject. Test therapeutic agents of the present invention may be screened from a plurality of chemical entities. The steps of screening for a therapeutic agent may be repeated with one or more compounds, e.g., with a library of compounds. For instance, the invention may feature a library comprising compounds or complexes that may treat or reduce the likelihood of pain the subject. Screening of multiple compounds can be carried out simultaneously or concurrently; or can be carried out simultaneously with some compounds and then concurrently with others. Therapeutic agents may include, pharmacological, non-pharmacological, and neuromodulatory agents as described herein.

Clinical Applications

In addition to using the methods of the present invention for determining that a subject (e.g., a mammal, e.g., a human) has a disease or disorder associated with the spinal cord and/or treating or reducing the likelihood of pain, the present methods may be used during invasive or surgical procedures (e.g., intraoperative, awake light sedation, or unconscious deep anesthesia), in particular if anesthetics or sedatives are contraindicated. Furthermore, the diagnostic methods of the present invention are useful for subjects or patients that are non-cooperative, in a non-communicating vegetative state, cognitively impaired, facing language barrier, or where verbal reporting is unreliable (e.g., in pediatric neonate subjects). Methods of the present invention may be Methods of the present invention also provide for safe, effective, and long-term treatment strategies for pain using, e.g., a neuromodulatory system for the relief of chronic pain. Such methods may include detecting electrical activity in a patient's brain to determine the occurrence of a biomarker of pain. The methods may also include providing therapeutic neurostimulation to the brain of the patient, e.g., at predefined times, frequencies, voltages, periodicities, and currents. For instance, these methods may involve electrodes implanted into a subject's brain, e.g., a deep brain stimulation system, electrodes on the scalp, e.g., a transcranial direct current stimulation system, and/or the use of magnetic stimulation, e.g., a transcranial magnetic stimulation system. The neurostimulation can be provided in response to detecting the presence of a biomarker of pain (e.g., a predefined pain biomarker) or on a periodic basis (e.g., every 1-2 hours). Methods of the present invention may also include the use of a transdermal patch placed on the skin for drug delivery or an intrathecal drug delivery pump for direct delivery of medication to the spinal cord.

EXAMPLES

Example 1. Spontaneous Oscillation in the Spinal Cord

Figure 1A:
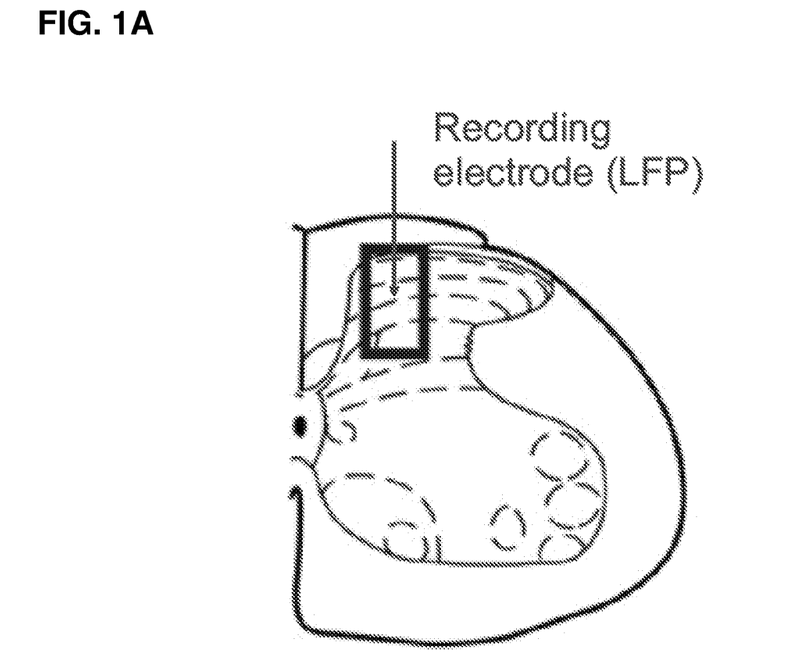
FIG. 1A is a schematic showing electrode placement in the spinal cord dorsal horn (L4) for the recoding of local field potential (LFP) from anesthetized rats (n=3 rats/group). Results are shown in B-D. CN2097 is an analgesic previously validated in the rat model (Neuroscience. 2010 May 5; 167(2):490-500. A cyclic peptide targeted against PSD-95 blocks central sensitization and attenuates thermal hyperalgesia. LeBlanc B W, Iwata M, Mallon A P, Rupasinghe C N, Goebel D J, Marshall J, Spaller M R, Saab C Y.) ibuprofen (400 mg/Kg) was administrated intraperitoneally, whereas CN2097 was administered as described in Leblanc et al.

This example demonstrates that spontaneous oscillation occurs in the spinal cord, which manifests at the electrophysiological level of local field potential (LFP). Experiments were conducted on anesthetized Sprague Dawley rats (200-250 g). As shown in FIG. 1A, LFP was recorded from the spinal cord dorsal horn lumbar 4 level in an anesthetized rat using a sharp microelectrode. LFP was sampled at a high frequency (25,000 Hz) and down-sampled offline to 250 Hz.

Example 2. Oscillation Modulated by Peripheral Nociceptive Events

Figure 1B:
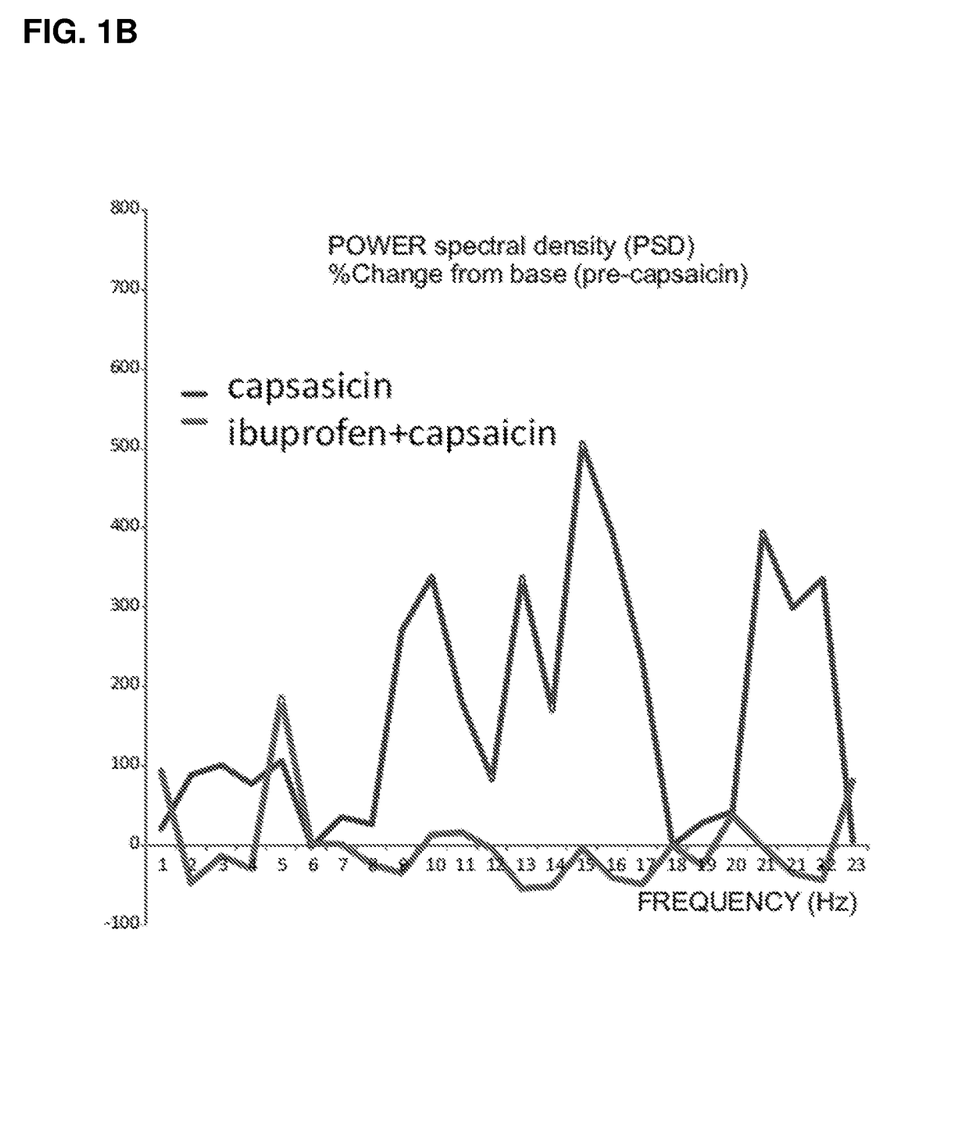
FIG. 1B is a graph showing enhanced power spectral density (PSD) versus frequency normalized to baseline (i.e. % change from baseline) in response to intradermal 5% capsaicin injection in the ipsilateral foot as a model of acute pain, and mitigation of the enhanced PSD by ibuprofen.
Figure 1C:
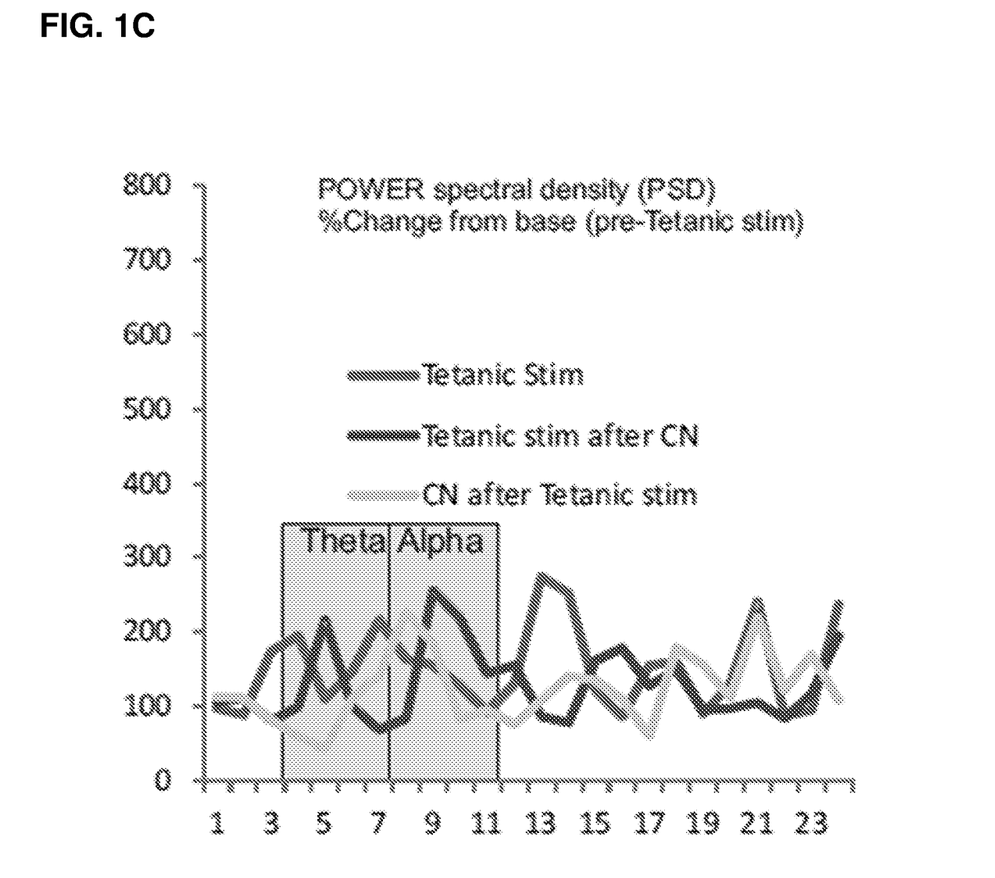
FIG. 1C is a graph showing PSD normalized to baseline after induction of long-term potentiation (LTP), a model of chronic pain, and before and/or after administration of an analgesic (CN2097).
Figure 1D:
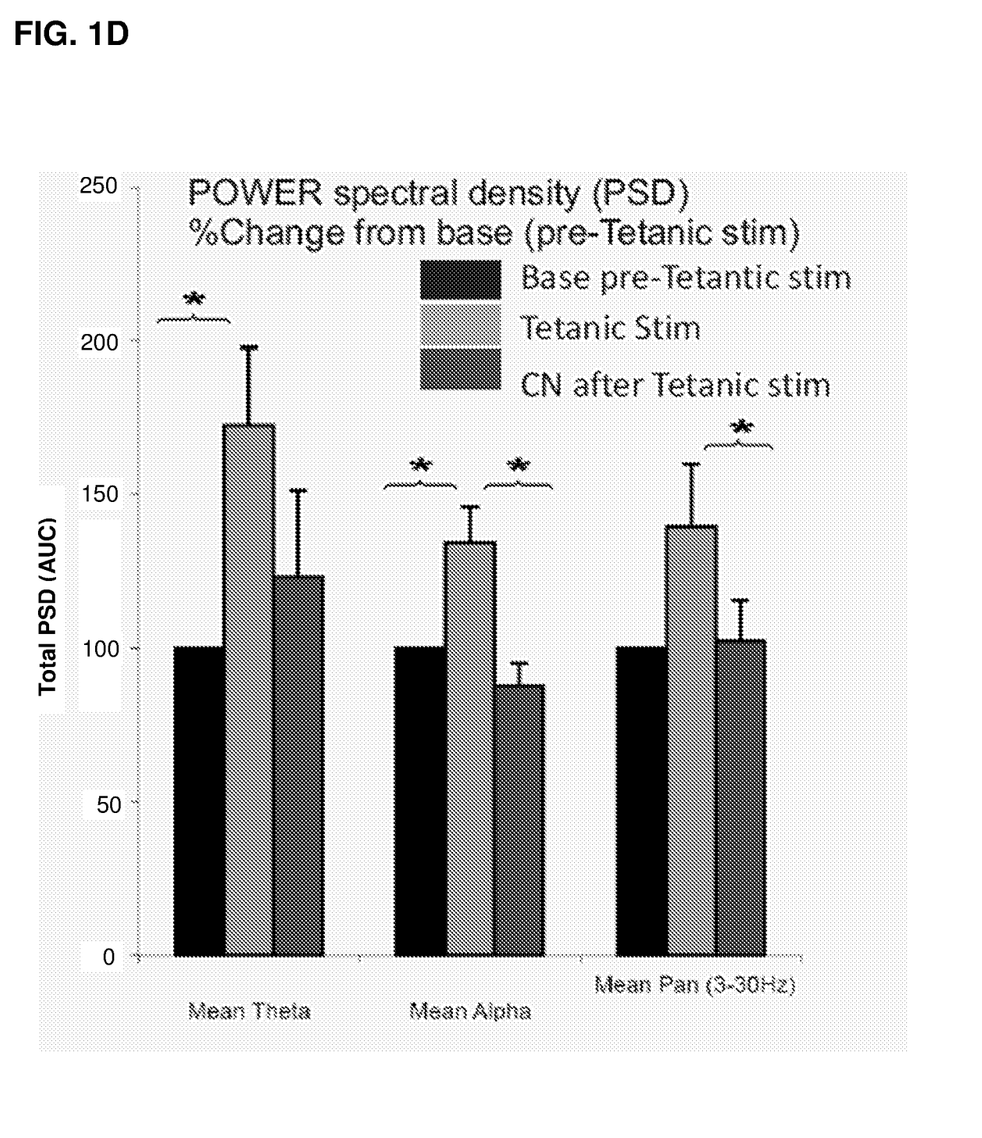
FIG. 1D is a graph showing PSD histograms derived from FIG. 1C of theta and alpha waveforms, as well as 3-30 Hz, at baseline, after induction of LTP, and after administration of an analgesic.

This example demonstrates that neuronal oscillation is modulated in the spinal cord dorsal horn by nociceptive events, such as pain-inducing agents. Natural sensory stimuli (e.g. brush and pinch) and intradermal injections of capsaicin were applied to the receptive field in the hindpaw corresponding to the recording site in the spinal cord. As shown in FIG. 1B, a fast Fourier transfer (FFT) function was applied using MATLAB® (MathWorks) to convert LFP waveforms from the time domain to the frequency domain, yielding power spectral density (PSD) histograms. PSD plots the distribution of the power amplitude of a waveform as a function of frequency. Spontaneous oscillation in the spinal cord dorsal horn was enhanced compared to baseline LFP recording in response to capsaicin injection in the ipsilateral foot within physiologically relevant frequency bands, e.g., theta and alpha, oscillated at baseline. As shown in FIG. 1C, PSD was modulated in response to electrical stimulation of the sciatic nerve at a tetanic, high-frequency voltage known to model a chronic nociceptive state. Neuronal oscillation increased in amplitude during LTP and reversed to normal after administration of an analgesic (e.g., CN2097). As shown in FIG. 1D, theta and alpha waveforms increased from baseline during LTP and reversed to normal after administration of the analgesic (e.g., CN2097). Thus, oscillation was normalized with systemic administration of an analgesic compound. These data provide the first evidence for spontaneous oscillation being modulated by peripheral nociceptive events and mitigated by analgesics.

OTHER EMBODIMENTS

Various modifications and variations of the described methods will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. A method for detecting neuronal oscillation in the spinal cord of a subject, said method comprising:
   a) recording local field potential (LFP) waveforms in the spinal cord of said subject;
   b) applying fast Fourier transfer (FFT) to convert LFP waveforms from the time domain to the frequency domain, thereby producing a power spectral density (PSD) histogram;
   c) assessing theta, alpha, beta, gamma, and/or newly identified frequency bands of said PSD histogram; and
   d) determining that said subject has a disease or disorder associated with the spinal cord, wherein an increase of one or more of said frequency bands from baseline, absence or occurrence of newly identified frequency bands, and/or shifts in peak amplitude or peak latency serves as an indicator of said disease or disorder.

2. The method of claim 1, further comprising administering a therapeutic agent to said subject.

3. The method of claim 1, wherein said disease or disorder associated with the spinal cord is selected from the group consisting of spinal cord ischemia, spinal cord convulsions, spinal cord infarction, spinal cord injury, disc herniation, multiple sclerosis, muscular dystrophy, amyotrophic lateral sclerosis, demyelinating diseases, bladder inflammation, irritable bowel syndrome, inflammatory bowel disease, breathing disorders, and esophageal disorders.

4. A method of treating or reducing the likelihood of pain in a subject by detecting neuronal oscillation in the spinal cord, said method comprising:
   a) recording LFP waveforms in the spinal cord of said subject;
   b) applying FFT to convert LFP waveforms from the time domain to the frequency domain, thereby producing a PSD histogram;
   c) assessing theta, alpha, beta, gamma, and/or newly identified frequency bands of said PSD histogram of said PSD histogram; and
   d) administering a therapeutic agent to said subject, if there is an increase of one or more of said frequency bands from baseline, absence or occurrence of newly identified frequency bands, and/or shifts in peak amplitude or peak latency.

5. The method of claim 4, wherein said pain is chronic pain.

6. The method of claim 5, wherein said chronic pain is selected from the group consisting of neuropathic pain, headache, migraine headache, chronic tension type headache, migraine with allodynia, joint pain, sinus pain, muscle pain, nerve pain, shoulder pain, pelvis pain, neck pain, back pain, arthritis, fibromyalgia, shingles, nerve damage, cancer, post-stroke pain, spinal cord injury, an inflammatory disease, reperfusion injury, inflammatory bowel disease, irritable bowel syndrome, bladder pain, referred pain, and head trauma.

7. The method of claim 4, wherein said pain is acute pain.

8. The method of claim 7, wherein said acute pain is nociceptive pain or post-operative pain.

9. The method of claim 1, wherein said LFP waveforms are recorded with one or more sensors positioned in the spinal cord of said subject.

10. The method of claim 1, wherein said LFP waveforms are recorded with one or more sensors attached to the skin of said subject.

11. The method of claim 1, wherein said LFP waveforms are recorded at sample frequencies between about 2 Hz to about 35,000 Hz.

12. The method of claim 1, further comprising recording brain activity of said subject.

13. The method of claim 12, wherein brain activity is recorded by electroencephalogram (EEG), magnetoencephalography (MEG), functional magnetic resonance imaging (fMRI), or positron emission tomography (PET).

14. The method of claim 1, further comprising treating said subject with a neuromodulatory system.

15. The method of claim 14, wherein said neuromodulatory system comprises a transcranial direct current stimulation system, transcranial magnetic stimulation system, or deep brain stimulation system.

16. The method of claim 14, wherein said neuromodulatory system comprises a transdermal patch or intrathecal drug delivery pump.

17. The method of claim 1, further comprising assessing an additional indicator of said disease or disorder, upon conversion of LFP to the frequency domain.

18. The method of claim 17, wherein said additional indicator is selected from the group consisting of signal coherence, cross-frequency coupling, and Granger causality.

19. The method of claim 1, wherein said LFP waveforms are recorded in the spinal cord dorsal horn of said subject.

* * * * *